(12) United States Patent
Chin

(10) Patent No.: US 6,669,729 B2
(45) Date of Patent: Dec. 30, 2003

(54) APPARATUS AND METHOD FOR THE REPLACEMENT OF POSTERIOR VERTEBRAL ELEMENTS

(76) Inventor: Kingsley Richard Chin, 2185 Cornell Rd., Cleveland, OH (US) 44106

( * ) Notice: Subject to any disclaimer, the term of this patent is extended or adjusted under 35 U.S.C. 154(b) by 0 days.

(21) Appl. No.: 10/364,847

(22) Filed: Feb. 11, 2003

(65) Prior Publication Data

US 2003/0171750 A1 Sep. 11, 2003

Related U.S. Application Data

(60) Provisional application No. 60/362,851, filed on Mar. 8, 2002.

(51) Int. Cl.[7] .................................................. A61F 2/44
(52) U.S. Cl. ............................... 623/17.11; 623/17.16; 606/61
(58) Field of Search ...................... 623/17.11, 17.12, 623/17.13, 17.14, 17.15, 17.16

(56) References Cited

U.S. PATENT DOCUMENTS

| | | | |
|---|---|---|---|
| 6,132,464 A | 10/2000 | Martin | |
| 6,352,537 B1 | 3/2002 | Strnad | |
| 6,419,703 B1 | 7/2002 | Fallin et al. | |
| 2002/0065557 A1 | 5/2002 | Goble et al. | |
| 2002/0072800 A1 | 6/2002 | Goble et al. | |

*Primary Examiner*—Cary E. O'Connor
*Assistant Examiner*—Candice C. Melson
(74) *Attorney, Agent, or Firm*—AKC Patents; Aliki K. Collins

(57) ABSTRACT

An orthopedic implantable device articulately connects a first spinal vertebra to an adjacent second spinal vertebra along the midline of the first and second vertebrae or along an axis medial to the facets. The device includes a first component having a male articulation member and a second component having a female articulation member. The first and second components are adapted to be attached to posterior locations of the first and the second vertebrae, respectively. The first component is articulately connected to the second component by engaging the male articulation member to the female articulation member or vice versa. The articulation mechanisms may be a hook and loop or a hinge. First and second components are configured to replace the natural lamina, spinous process, pars interarticularis, and/or facets of the corresponding first and second vertebrae.

29 Claims, 9 Drawing Sheets

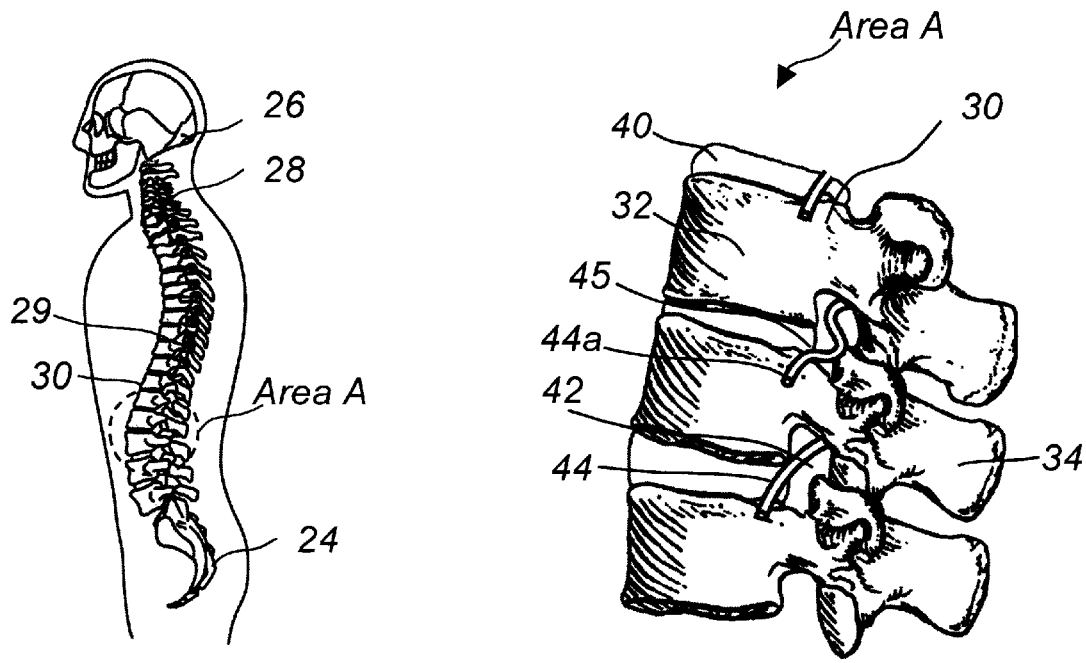
FIG. 1A
FIG. 1B
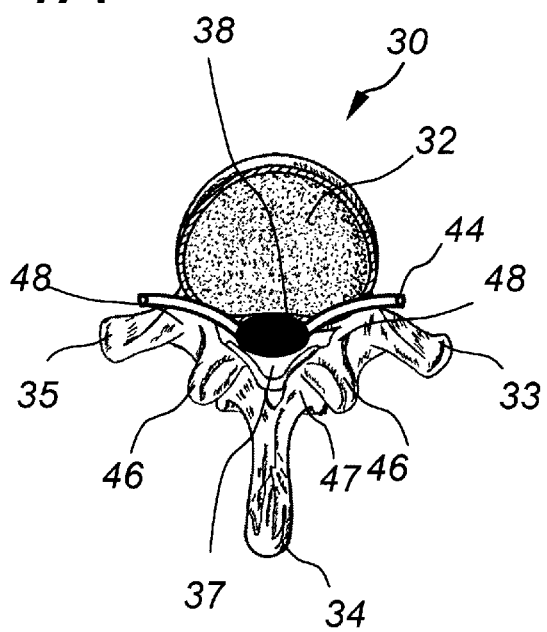
FIG. 1C

APPARATUS AND METHOD FOR THE REPLACEMENT OF POSTERIOR VERTEBRAL ELEMENTS

CROSS REFERENCE TO RELATED CO-PENDING APPLICATIONS

This application claims the benefit of U.S. provisional application Ser. No. 60/362,851 filed on Mar. 8$^{th}$, 2002 and entitled SPINOUS PROCESS, LAMINA, AND FACET REPLACEMENT APPARATUS which is commonly assigned and the contents of which are expressly incorporated herein by reference.

FIELD OF THE INVENTION

The present invention relates to an apparatus and a method for the replacement of posterior vertebral elements, and more particularly to an apparatus and a method that replaces posterior vertebral elements while preserving spinal stability and mobility.

BACKGROUND OF THE INVENTION

The human spine 29 comprises individual vertebrae 30 that interlock with each other to form a spinal column, shown in FIG. 1A. Referring to FIGS. 1B, 1C, and 1D, each vertebra 30 has a cylindrical bony body (vertebral body) 32, two pedicles 48 extending from the vertebral body 32, a lamina 47 extending from the pedicles 48, three winglike projections (two transverse processes 33, 35 extending from the pedicles 48 and one spinous process 34 extending from the lamina 47), pars interarticularis 36, two superior facets 46 extending from the pedicles 48 and two inferior facets 45 extending from the lamina 47. The pars interarticularis 36 connects the superior 46 and inferior 45 facets on either side of the spinous process 34. The bodies of the vertebrae 32 are stacked one on top of the other and form the strong but flexible spinal column. The spinous process 34, lamina 47, pars interarticularis 36, superior facets 46, inferior facets 45, transverse processes 33, and pedicles 48 are positioned so that the space they enclose forms a tube, i.e., the spinal canal 37. The spinal canal 37 houses and protects the spinal cord and other neural elements. A fluid filled protective membrane, the dura 38, covers the contents of the spinal canal. The spinal column is flexible enough to allow the body to twist and bend, but sturdy enough to support and protect the spinal cord and the other neural elements.

The vertebrae 30 are separated and cushioned by thin pads of tough, resilient fiber known as inter-vertebral discs 40. Inter-vertebral discs 40 provide flexibility to the spine and act as shock absorbers during activity. There is a small opening (foramen) 42 between each vertebra 30, through which nerves 44 pass and go to different body parts. When the vertebrae are properly aligned the nerves 44 pass through without a problem. However, when the vertebrae are misaligned or a constriction 45 is formed in the spinal canal, the nerves get compressed 44a and may cause back pain, leg pain or other neurological disorders. Disorders of the spine that may cause misalignment of the vertebrae or constriction of the spinal canal include spinal injuries, infections, tumor formation, herniation of the inter-vertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina 47, i.e., the bony roof of the spinal canal. Discectomy involves removal of the inter-vertebral discs 40. Corpectomy involves removal of the vertebral body 32 as well as the adjacent disc spaces 40. Laminectomy and corpectomy result in central exposure of the dura 38 and its contents. An exposed dura 38 puts the neural elements and spinal cord at risk from direct mechanical injury or scarring from overlying soft tissues. Scarring is considered a major cause for failed back syndrome in which patients continue to have back and leg pain after spinal surgery. Current methods to decrease the risk of developing this syndrome include covering the dura with fat harvested from the patient's subcutaneous tissues or using a synthetic material. However, no material as yet has been used that completely or significantly prevents scarring of the dura and nerve roots after spine surgery in humans.

Furthermore, laminectomy predisposes the patient to instability through the facet joints and may lead to post-laminectomy kyphosis (abnormal forward curvature of the spine), pain, and neurological dysfunction. Therefore the surgeon needs to stabilize the spine after laminectomy procedures and after corpectomy. One spine stabilization method is fusion. Fusion involves the fixation of two or more vertebrae. Fusion works well because it stops pain due to movement of the intervertebral discs 40 or facets 45, 46, immobilizes the spine, and prevents instability and or deformity of the spine after laminectomy or corpectomy. However, spinal fusion limits spinal mobility. Maintaining spinal mobility may be preferred over fusion in some cases to allow more flexibility of the spine and to decrease the risk of junction problems above and below the level of the fixation due to increased stress.

An arthritic facet joint may also cause back pain. Since the majority of the motion along the spine occurs at the facet joints, fusing the diseased facet would often relieve pain but again at a high cost of fusing across at least one spinal segment thus preventing motion and effectively increasing stresses at the adjacent facet joints. Increased stresses predispose facet joints to accelerated arthritis, pain, and instability requiring additional surgery to fuse these levels. This cyclic process results in an overall decreased mobility of the spine. Therefore, it is an attractive alternative to attempt to replace the diseased facet without resorting to fusion, thus avoiding significant limitation in mobility of the spine. The obvious solution would be to replace the opposing surfaces of each facet to preserve motion between the surfaces. Any efforts to replace the facets at their natural location necessitate destroying the facet capsule and risks producing an unstable joint. It would be desirable to achieve spine stabilization that preserves mobility, protects the contents of the spinal canal, does not cause tissue scarring, decreases pain in the facet joints, and does not always destroy the facet capsule.

SUMMARY OF THE INVENTION

In general, in one aspect, the invention features an orthopedic implantable device articulately connecting a first spinal vertebra to an adjacent second spinal vertebra. Each spinal vertebra includes a vertebral body, a pair of pedicles extending posteriorly from the vertebral body, a lamina extending from the pedicles, a pair of superior facets extending from the pedicles, a pair of inferior facets extending from the lamina, a pair of pars interarticularis connecting the superior and inferior facets, a spinous process extending from the lamina and a pair of transverse processes extending from the pedicles. The orthopedic implantable device includes a first component adapted to be attached to a posterior location of the first vertebra and a second component adapted to be attached to a posterior location of the second vertebra. The first component is articulately connected to the second component.

Implementations of this aspect of the invention may include one or more of the following features. The first component may be articulately connected to the second component along a posterior midline of the first and second vertebrae and/or along an axis medial to the facets of the vertebrae. The first component may comprise a body and at least one male articulation member attached to the first component body and the second component may comprise a body and at least one female articulation member attached to the second component body and the first component may be articulately connected to the second component by engaging the at least one male articulation member to the at least one female articulation member. The at least one male articulation member may comprise a hook and the at least one female articulation member may comprise a loop. The first component body may further comprise at least one female articulation member and the second component body may further comprise at least one male articulation member. The posterior locations of the first and second vertebrae are selected from a group including a pedicle, transverse processes, facets, lamina, pars interarticularis, and vertebral body. The body of the first component may be attached to first and second pedicles of the first vertebra and the body of the second component may be attached to first and second pedicles of the second vertebra, respectively. The first and second components may be attached to the first and second vertebrae, respectively, via screws, wires, or hooks. The first component may be articulately connected to the second component via a hinge. The first and second components may have adjustable width and the width may be adjusted between 20 and 80 millimeters.

In general, in another aspect, the invention features an orthopedic implantable device articulately connecting a plurality of individual vertebrae. The vertebrae are adjacent to each other and form a segment of a spinal column. The orthopedic device includes a plurality of individual components, and each component is adapted to be attached to a posterior location of an individual vertebra. Each of the individual components is articulately connected to an adjacent inferior and an adjacent superior component along a posterior midline of the spinal column or any axis medial to the facets.

Implementations of this aspect of the invention may include one or more of the following features. Each component may comprise a body, at least one female articulation member formed within the body, and at least one male articulation member attached to the body. Each of the individual components may be articulately connected to an adjacent inferior component by engaging the at least one male articulation member to the at least one female articulation member of the adjacent inferior component, and each of the individual components may be articulately connected to an adjacent superior component by engaging the at least one female articulation member to the at least one male articulation member of the superior component.

In general, in another aspect, the invention features an orthopedic implantable component adapted to replace a posterior element of a vertebra. The vertebra comprises a vertebral body, a pair of pedicles extending posteriorly from the vertebral body, a lamina extending from the pedicles, a pair of superior facets extending from the pedicles, a pair of inferior facets extending from the lamina, a pair of pars interarticularis connecting the superior and inferior facets, a spinous process extending from the lamina and a pair of transverse processes extending from the pedicles. The orthopedic component includes a body adapted to be attached to a posterior location of the vertebra, a male articulation member extending from the body, and a female articulation member formed within the body.

Implementations of this aspect of the invention may include one or more of the following features. The body may be configured to replace the lamina, the spinous process, pars interarticularis, and the superior and inferior facets of the vertebra. The body may be attached to the pedicles of the vertebra via screws threaded through apertures formed in the body. The screws may be made of stainless steel, titanium, gold, silver, alloys thereof, plastic, absorbable or biodegradable material. The orthopedic implantable component may be made of metal, plastic, ceramic, bone, polymers, composites, absorbable material, biodegradable material, and combinations thereof. The male articulation member may be a hook and the female articulation member may be a bar connecting opposite sides of a cavity formed within a bottom surface of the body. The cavity may be arranged along a midline of the body or along any axis medial to the facets.

In general, in another aspect, the invention features a spine stabilization method articulately connecting a first vertebra to a second vertebra including the following steps. First providing a first component and attaching the first component to a posterior location of the first vertebra. Next, providing a second component and attaching the second component to a posterior location of the second vertebra. Finally, articulately connecting the first component to the second component.

In general, in another aspect, the invention features a spine stabilization method connecting a first vertebra to a second vertebra including the following steps. First attaching first and second screws to first and second locations, respectively, of the first vertebra. Next attaching third and fourth screws to first and second locations, respectively, of the second vertebra. Next providing first and second components, the first and second components comprising a body and being articulately connected to each other along a midline of the bodies. Next attaching the body of the first component to the first and second locations of the first vertebra via the first and second screws, respectively. Next, attaching the body of the second component to the first and second locations of the second vertebra via the third and fourth screws, respectively. Finally, tightening of all said screws.

Implementations of this aspect of the invention may include before attaching the bodies of the first and second components adjusting the width of the bodies of the first and second components.

Among the advantages of this invention may be one or more of the following. The implantable spinal stabilization device stabilizes the spine, while allowing the patient to retain spinal flexibility by preserving motion between adjacent vertebras. The spinal stabilization device may be used for the treatment of a multitude of spinal disorders including facet arthritis and spinal stenosis. The device covers and protects the posterior central neural elements after laminectomy, and replaces diseased or injured facet joints without fusing across vertebral segments. The invention can be used to replace the spinous process, laminas, and facets individually or in combination at each vertebra. The implantable device has a compact structure and low profile. By virtue of transferring the motion between adjacent vertebras from the diseased or iatrogenically injured facets laterally towards the midline, the spine is stabilized but also allows motion between the vertebrae. This is a desirable feature when compared to fusion in selected cases where preserving a patient's spinal mobility is preferred.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views:

FIG. 1A is a side view of the human spinal column;

FIG. 1B is an enlarged view of area A of FIG. 1A;

FIG. 1C is an axial cross-sectional view of a lumbar vertebra;

DETAILED DESCRIPTION OF THE INVENTION

Figure 1D:
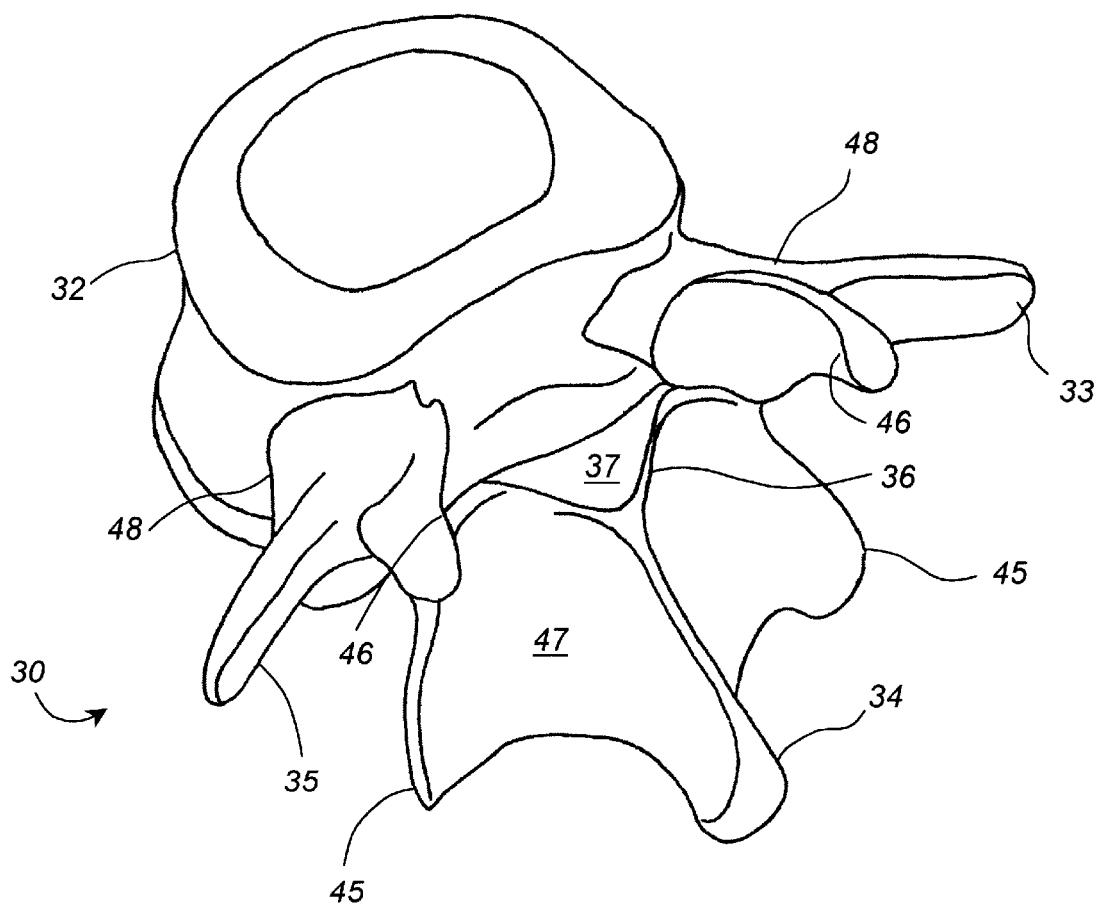
FIG. 1D is a perspective view of a lumbar vertebra.
Figure 2:
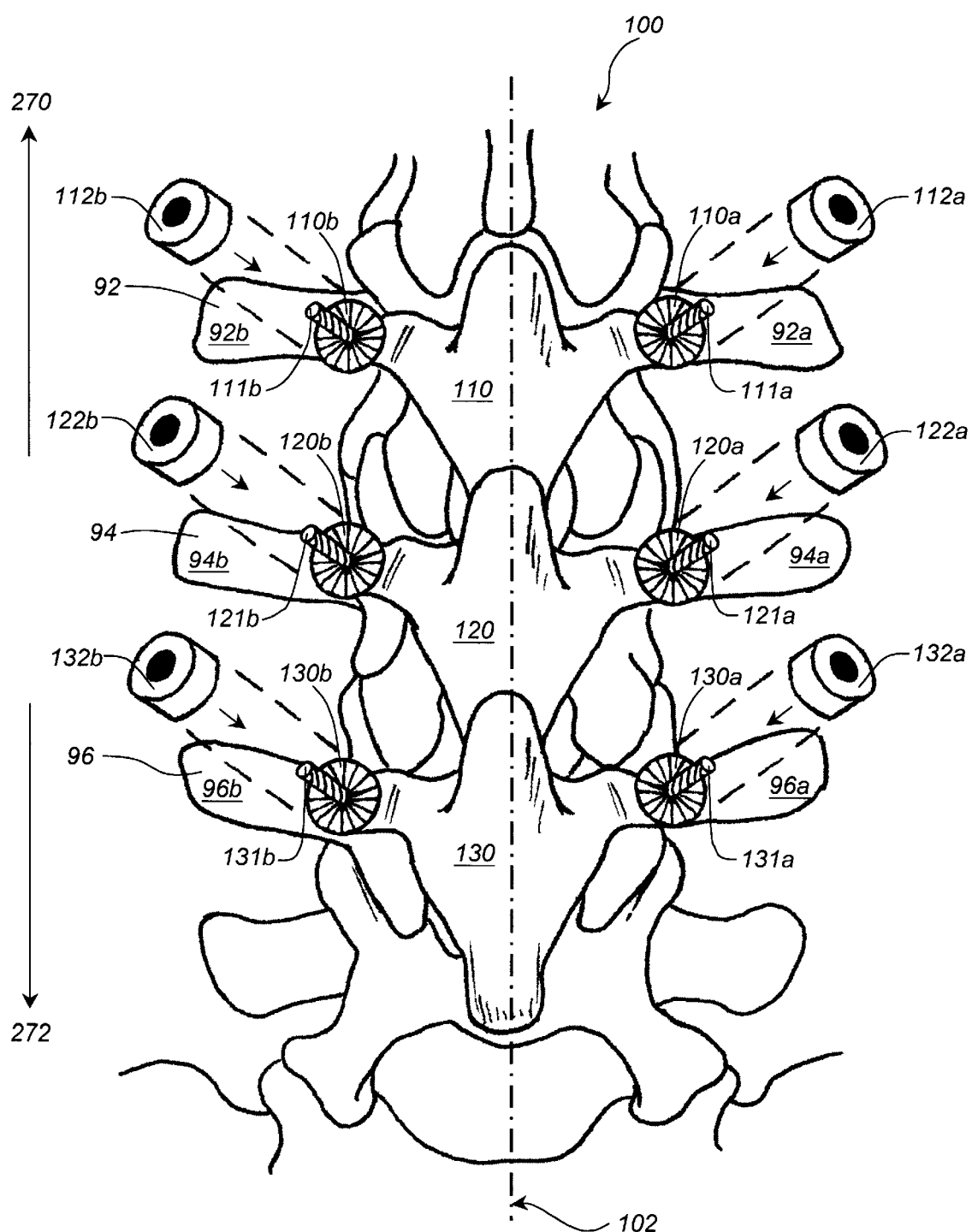
FIG. 2 is a schematic posterior view of an implantable spine stabilization device according to this invention.

Referring to FIG. 2, an implantable spine stabilization device 100 connects vertebra 92 to adjacent vertebra 94 and vertebra 94 to adjacent vertebra 96. The spine stabilization device 100 includes modular components 110, 120, and 130. Modular components 110, 120, and 130 have circular ends 110a and 110b, 120a and 120b, 130a and 130b, respectively, that attach to pedicles 92A, 92B, 94A, 94B, 96A, and 96B of vertebra 92, 94 and 96, respectively, via pedicle screws 111a, 111b, 121a, 121b, 131a, and 131b, respectively. Modular components 110, 120, and 130 replace the resected laminas, pars interarticularis, facets and spinous processes of the vertebra 92, 94, and 96, respectively. Modular component 110 is articulately connected to component 120 along the midline 102 of the device 100 and the corresponding vertebrae 92 and 94, shown in FIG. 6. Similarly modular component 120 is articulately connected to component 130. Additional modular components may be added to extend the spine stabilization device 100 in either caudad 272 or cephalad 270 directions. The modular structure of the spine stabilization device 100 allows a surgeon to replace laminas, facets, pars interarticularis, and spinous processes over any distance and orientation along the entire spine 29.

Figure 3:
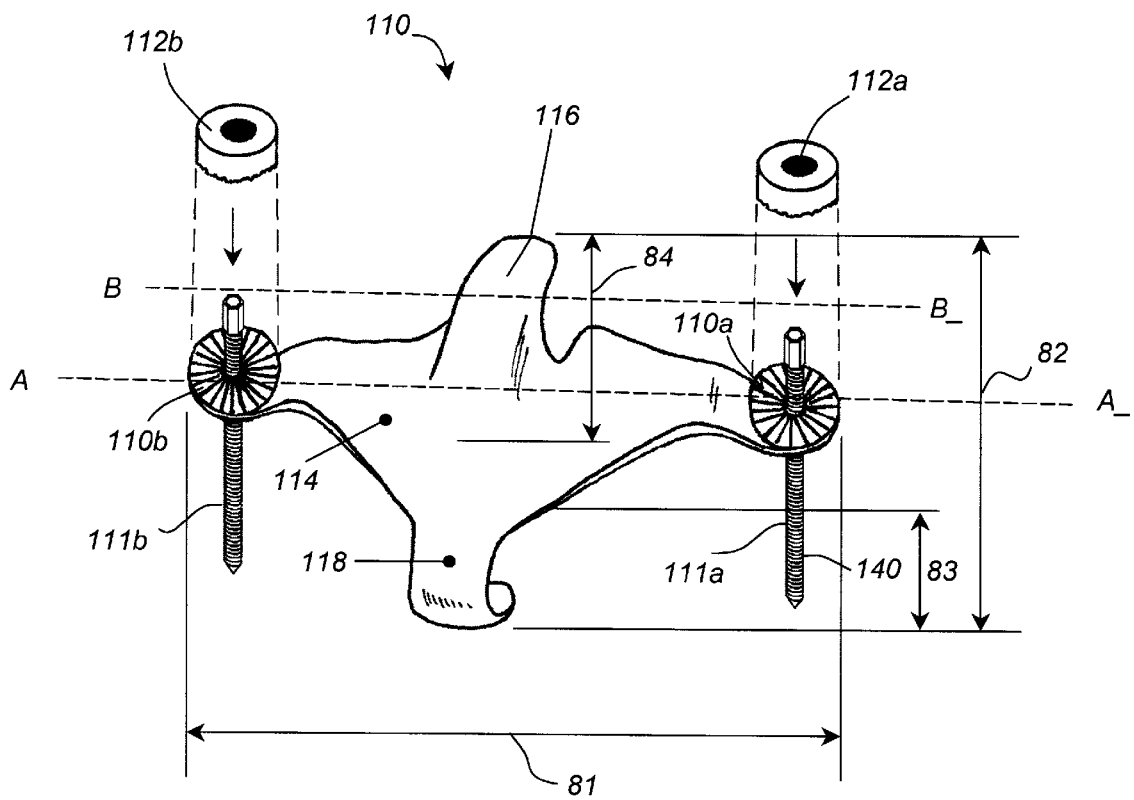
FIG. 3 is a posterior view of a spine stabilization component of the implantable spine stabilization device of FIG. 3.

Referring to FIG. 3, modular component 110 comprises a lamina 114, two circular ends 110a, 110b extending laterally from opposite sides of the lamina 114, a tail segment 118 extending from the lower portion of the lamina 114, and a spinous process 116 protruding posteriorly from the top surface of the lamina 114. The lamina 114 has a width 81 and a length 82 that depend upon the distance between the pedicles 92A and 92B and the length of the vertebra 92, respectively. The length 83 of the tail segment 118 depends upon the intervertebral distances. In one example, the width 81 is in the range between 20 millimeters and 80 millimeters, length 82 is in the range of 10 millimeters and 80 millimeters, length 83 is in the range of 4 millimeters and 60 millimeters and height 84 is in the range of 4 millimeters and 30 millimeters. Width 81, length 82, length 83 and height 84 have different values for the different type of vertebrae, including lumbar, thoracic, sacral and cervical.

Figure 5:
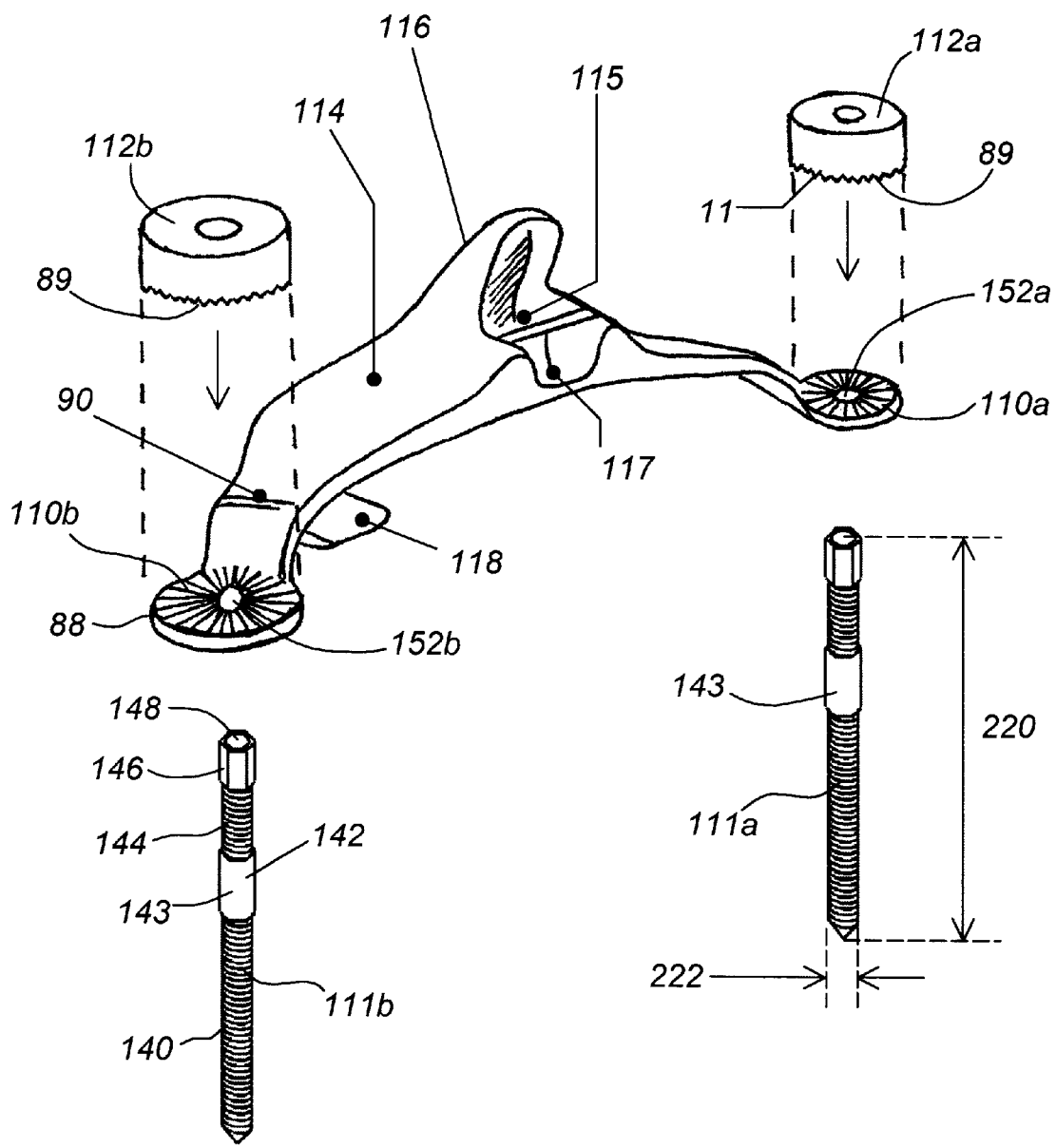
FIG. 5 is a perspective view of the spine stabilization component of FIG. 3.

Referring to FIG. 3 and FIG. 5, pedicle screw 111b comprises a body portion 140, a first head portion 142, a second head portion 144, and a head 146. The body portion 140 of the pedicle screw 111b has helical threads on its exterior surface and screws into the vertebral body 32 through the pedicle 92B. A hexagonal screwdriver (not shown) is inserted into a slot 148 formed on the head 146 of the pedicle screw 111b and is used to drive the screw 111b into the vertebral body 32. The first head portion 142 is directly above the body portion 140 and has a smooth or serrated outer surface 143 for receiving the circular end 110b of modular component 110. End 110b has an aperture 152b that allows end 110b to slide over the pedicle screw 111b. The second head portion 144 has a threaded outer surface for receiving locking nut 112b. Locking nut 112b slides over the head 146 of the pedicle screw 111b and screws around the threaded outer surface of the second head portion 144, thus securely attaching the circular end 110b to pedicle screw 111b. In one example, pedicle screw 111a has a length 220 of 57 millimeters and a diameter 222 of 6.5 millimeters.

Figure 4:
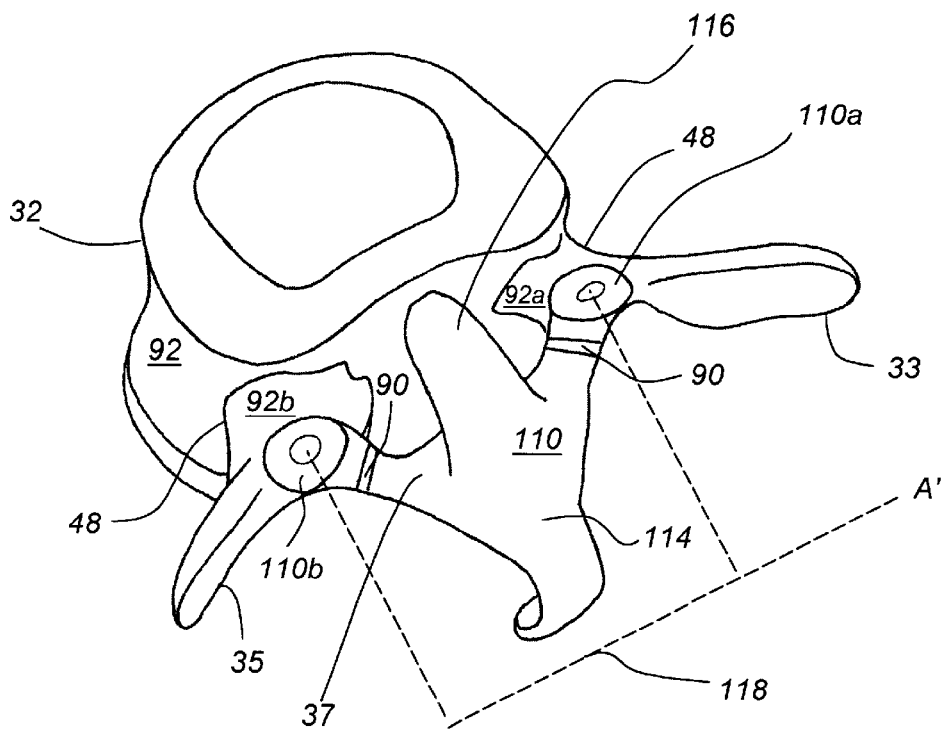
FIG. 4 is a perspective view of a lumbar vertebra with resected spinous process, lamina, and facet joints and the stabilization component of FIG. 3 attached to its pedicles.
Figure 4A:
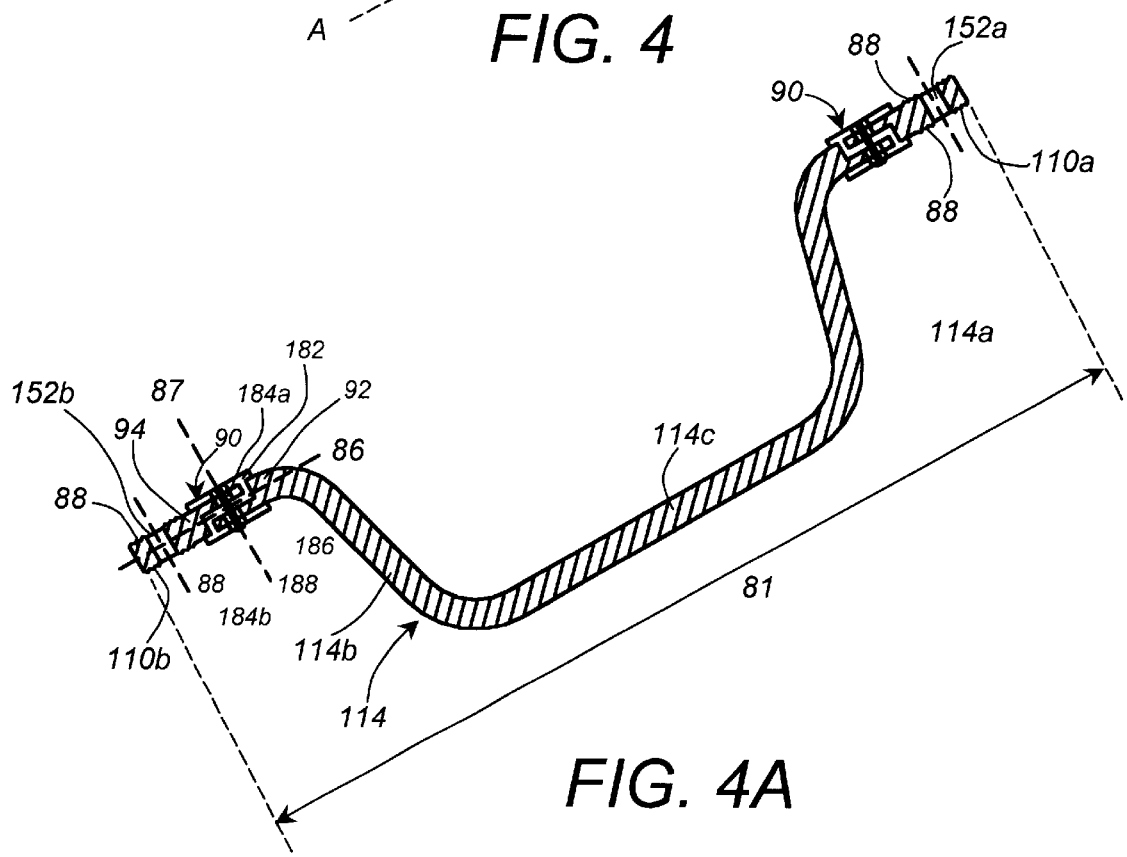
FIG. 4A is a cross-sectional view of FIG. 3 along AA' plane.

Referring to FIG. 4 and FIG. 4A, the cross-section of lamina 114 along AA' has a U-shape and the roof 114c of the lamina (top of U-shape) is elevated above the spinal canal 37. The sides 114a and 114b of the lamina 114 run first at a gentle slope downwards about 5 degrees and then drop more sharply at about 80 degrees to get to the pedicles 92A and 92B, respectively. The U-shape form of the lamina 114 provides space between the spine stabilization device 100 and the spinal canal 37 and is also designed to clear the facets 46 laterally, in case they were not previously resected. This arrangement covers the central spinal canal and protects the neural elements from scar tissue formation or mechanical damage. The lamina 114 has a flared lower portion that extends into the tail segment 118.

In the embodiment of FIG. 4A the width 81 of the lamina 114 is extended or contracted via mechanism 90. In this embodiment the lamina 114 comprises a first segment 92 and a second segment 94. Segment 94 is allowed to slide in the lateral direction 86 and can rotate around the axis 87. The lateral motion of segment 94 allows the adaptation of the modular component 110 to vertebrae with various pedicle distances. The rotation of segment 94 around the axis 87 allows accurate positioning of the circular end 110b over the pedicle screw 111b and accommodates pedicles that are not perfectly aligned in the cephalo-caudad direction. Segments 94 and 92 have overlapping elongated slots 184A and 184B, respectively, extending through the thickness of the corresponding segment. A housing 182 slides over the overlapping segments 92 and 94. Housing 182 has an elongated slot 186 that runs through the thickness of the housing 182 and is aligned with the elongated slots 184A and 184B. The position of the overlapping segments 92 and 94 and the housing 182 is secured via a screw 188 that is threaded through the elongated slots 184A, 184B, and 186. In one example, the width 81 of the lamina 114 is 40 millimeters and it can be increased or decreased up to 8 millimeters via the two sliding mechanisms 90. Circular ends 110a, 110b have apertures 152a, 152b, respectively. Apertures 152a and 152b have serrated inner surfaces for receiving a pedicle screw with matching longitudinal serrations 143, shown in FIG. 5. The top and/or bottom surfaces of circular ends 110a, 110b have radial extending grooves 88 that match the grooves 89 of the locking nuts 112a, 112b.

Figure 5A:
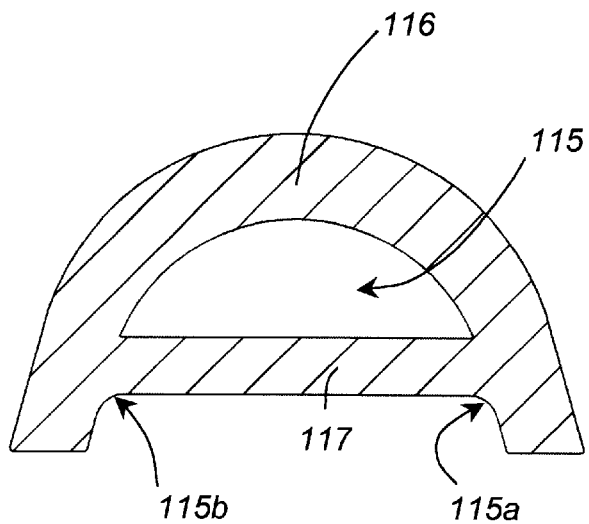
FIG. 5A is a cross-sectional view of FIG. 3 along BB' plane.
Figure 6:
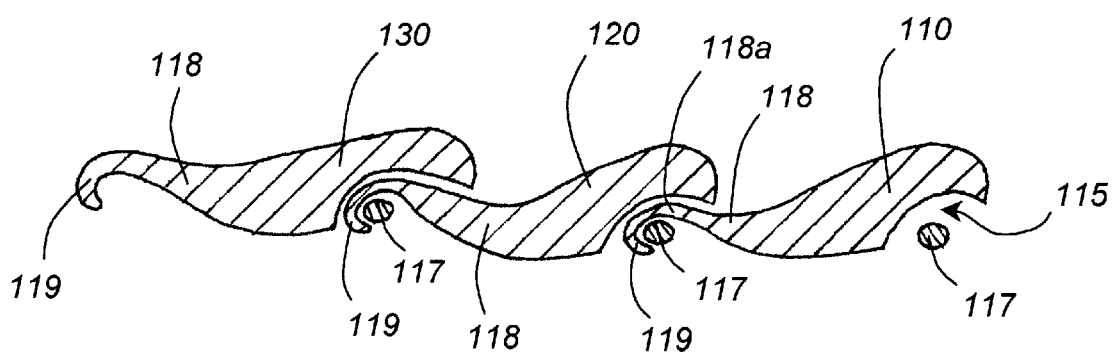
FIG. 6 is a cross-sectional side view of the spine stabilization device of FIG. 2 along midline 102.

Referring to FIG. 5 and FIG. 5A, the posteriorly protruding spinous process 116 includes a cavity 115 formed in the bottom surface of the lamina 114 within the spinous process 116. Inside the cavity 115 there is a horizontally extending bar 117 attached to opposite cavity walls 115a, 115b. Referring to FIG. 6, the end of the tail segment 118 of modular component 110 forms a hook 119. Hook 119 engages around the horizontal bar 117 of the adjacent modular component 120 and forms an articulated connection between the two modular components 110 and 120. The cavity 115 is contoured to allow smooth gliding of the outer surface 118a of the tail segment 118 around the horizontal bar 117.

Figure 7:
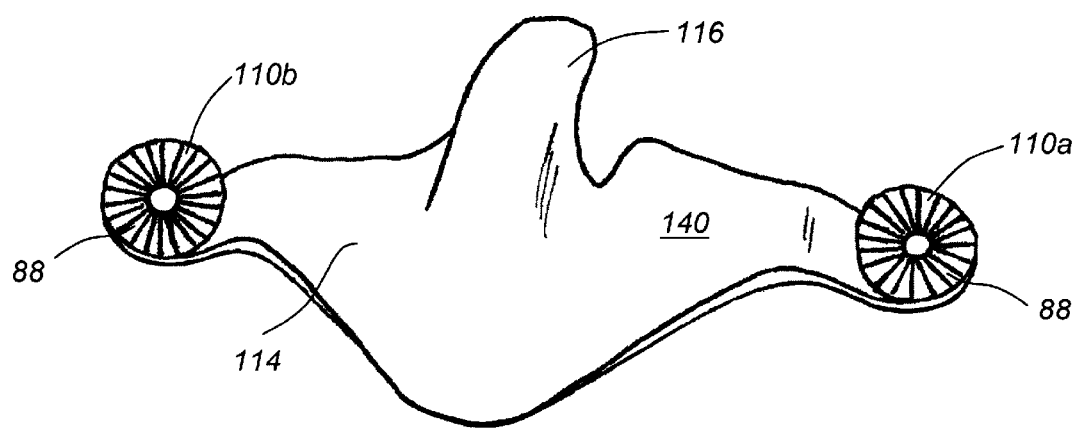
FIG. 7 is a posterior view of a spine stabilization component without a tail segment.

Referring to FIG. 7, a modular component 140 without the tail segment 118 is implanted to the pedicles on the vertebra that is below but adjacent to the lowest (in the caudad direction 272) level that underwent either a laminectomy or facetectomy. This vertebra will still have its natural spinous process and ligamentous attachment to the next lower vertebra. This vertebral level will therefore provide stability to the end of the stabilization assembly 100 since this vertebral level will have preserved facets and ligamentous attachments.

Figure 8:
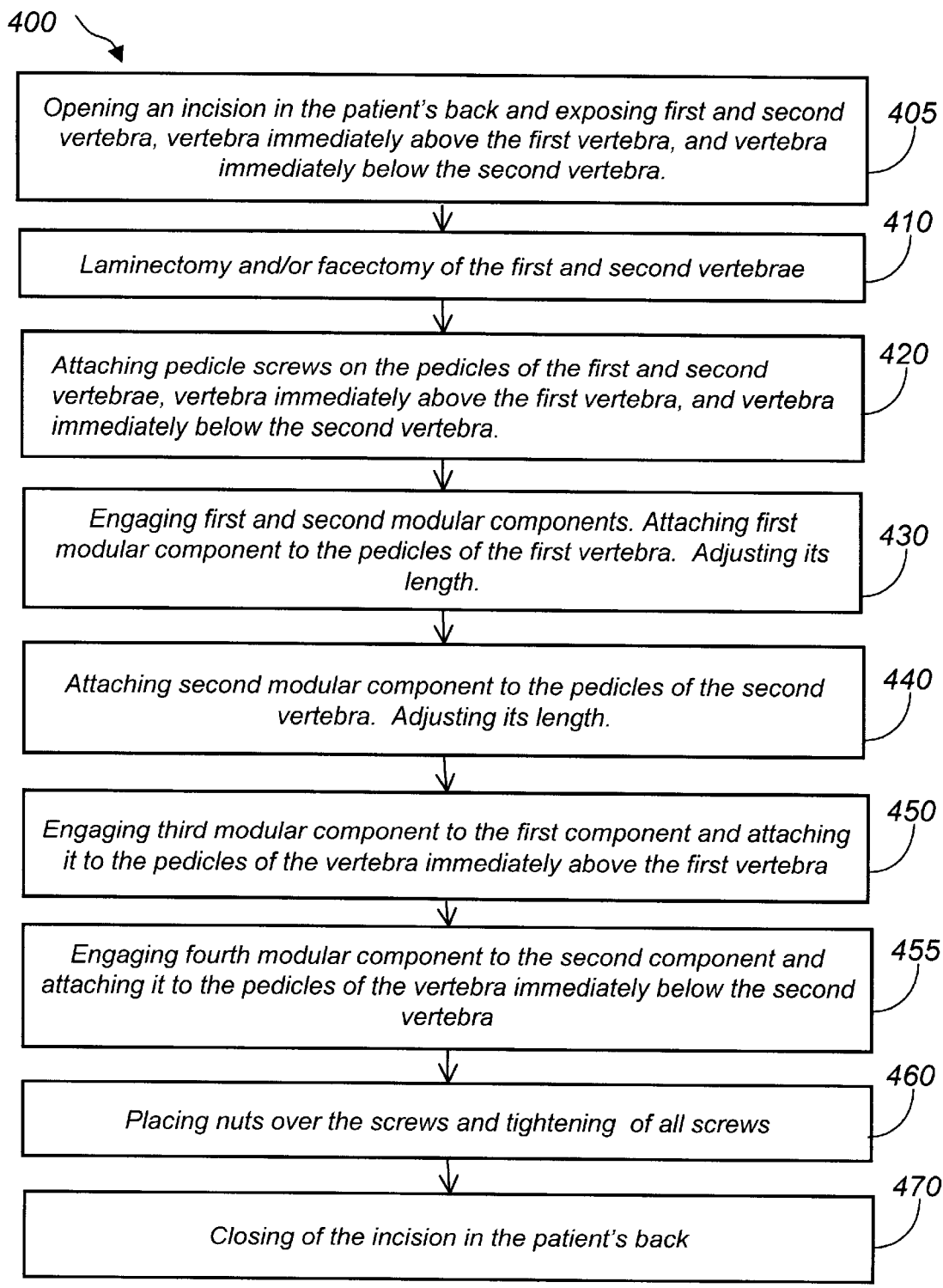
FIG. 8 is a flow diagram depicting the method of applying the implantable spine stabilization device of this invention.

Referring to FIG. 8, a method 400 of using the spine stabilization device 100 comprises the following steps. Opening an incision in the patient's back, and exposing first and second vertebrae, the vertebra that is immediately above but adjacent to the first vertebra (cephalad direction), and the vertebra that is immediately below but adjacent to the second vertebra (caudad direction) (405). Performing laminectomy and/or facetectomy posteriorly of the first and second vertebrae (410). Placing pedicle screws within the pedicles of the first and second vertebra, the vertebra immediately above the first vertebra, and the vertebra immediately below the second vertebra (420). Engaging a first modular component to a second modular component. In one example, the modular components are as shown in FIG. 3. Placing the apertures of the two circular ends 110a, 110b of the first modular component over the two contralateral pedicle screws on the first vertebra, and adjusting the length and orientation of the two end segments 94 of the lamina (430). Placing the apertures of the two circular ends 110a, 110b, of the second modular component over the two contralateral pedicle screws on the second vertebra, and adjusting the length and orientation of the two end segments 94 of the lamina (440). Engaging a third modular component without a tail segment, as shown in FIG. 7, to the tail of the second modular component, placing the apertures of the two circular ends 110a, 11ab, of the third modular component over two contralateral pedicle screws on the vertebra that is immediately below the second vertebra, and adjusting the length and orientation of the two end segments 94 of the lamina (450). Engaging a fourth modular component to the first modular component, placing the apertures of the two circular ends 110a, 110b, of this fourth modular component over the two contralateral pedicle screws on the vertebra that is immediately above the first vertebra, and adjusting the length and orientation of the two end segments 94 of the lamina (455). Tightening of the nuts over the pedicle screws down on the circular ends (460) and closing of the incision in the patient's back (470).

Other embodiments are within the scope of the following claims. For example, the articulation mechanism between the modular components may be a hinge. There may be more than one articulation mechanisms medial or lateral to the medial line 102 on a given vertebra, and/or medial to both the natural facet joints. The ends of the modular components may be secured to pedicle screws via connectors. The ends of the modular components may be attached to the vertebrae via hooks. Other locations where screws, wires, or hooks may be anchored for attaching the stabilization device of this invention include the transverse processes 33, 35, the vertebral body 32, and the lamina 47. The modular components may be solid without adjustable ends. Modular components 110, 120, 130 and 140 may be manufactured from a variety of materials including among others stainless steel, titanium, nickel, composites, ceramics, plastic, bone, bioabsorbable material or combination thereof. Pedicle screws may be manufactured from a variety of materials including among others stainless steel, titanium, gold, silver ceramics, plastic, bioabsorbable material, or alloys thereof.

Several embodiments of the present invention have been described. Nevertheless, it will be understood that various modifications may be made without departing from the spirit and scope of the invention. Accordingly, other embodiments are within the scope of the following claims.

What is claimed is:

1. An orthopedic implantable device articulately connecting a first spinal vertebra to an adjacent second spinal vertebra wherein each spinal vertebra comprises a vertebral body, a pair of pedicles extending posteriorly from said vertebral body, a lamina extending from said pedicles, a pair of superior facets extending from said pedicles, a pair of inferior facets extending from said lamina, a pair of pars interarticularis connecting superior and inferior facets, a spinous process extending from said lamina and a pair of transverse processes extending from said pedicles comprising:

a first component adapted to be attached to a posterior location of said first vertebra;

a second component adapted to be attached to a posterior location of said second vertebra; and wherein said first component comprises a body and at least one male articulation member attached to said first component body and said second component comprises a body and at least one female articulation member attached to said second component body and wherein said first component is articulately connected to said second component by engaging said at least one male articulation member to said at least one female articulation member.

2. The orthopedic implantable device of claim 1 wherein said first component is articulately connected to said second component along a posterior midline of said first and second vertebrae.

3. The orthopedic implantable device of claim 1 wherein said first component is articulately connected to said second component along an axis medial to said facets of said vertebrae.

4. The orthopedic implantable device of claim 1 wherein said at least one male articulation member comprises a hook and said at least one female articulation member comprises a loop.

5. The orthopedic implantable device of claim 1 wherein said first component body further comprises at least one female articulation member.

6. The orthopedic implantable device of claim 1 wherein said second component body further comprises at least one male articulation member.

7. The orthopedic implantable device of claim 1 wherein said posterior locations of said first and second vertebrae are selected from a group consisting of a pedicle, transverse processes, facets, pars interarticularis, intervertebral disc, lamina, and vertebral body.

8. The orthopedic implantable device of claim 1 wherein said body of said first component is attached to first and second pedicles of said first vertebra and said body of said second component is attached to first and second pedicles of said second vertebra, respectively.

9. The orthopedic implantable device of claim 1 wherein said first and second components are attached to said first and second vertebrae, respectively, via connectors selected from a group consisting of screws, wires, and hooks.

10. The orthopedic implantable device of claim 1 wherein said first component is articulately connected to said second component via a hinge.

11. The orthopedic implantable device of claim 1 wherein said first and second components have adjustable width.

12. The orthopedic implantable device of claim 11 wherein said width of said first and second components can be adjusted between 20 and 80 millimeters.

13. The orthopedic implantable device of claim 1 wherein said first or second vertebrae are selected from a group consisting of cervical, thoracic, lumbar and sacrum vertebrae.

14. An orthopedic implantable device articulately connecting a plurality of individual vertebrae, wherein said vertebrae are adjacent to each other and form a segment of a spinal column, comprising:
a plurality of individual components, wherein each component is adapted to be attached to a posterior location of an individual vertebra; and
wherein each of said individual components comprises a body, at least one female articulation member formed within said body, and at least one male articulation member attached to said body: wherein each of said individual components is articulately connected to an adjacent inferior component by engaging its said at least one male articulation member to said at least one female articulation member of said inferior component; and wherein each of said individual components is articulately connected to an adjacent superior component by engaging its said at least one female articulation member to said at least one male articulation member of said superior component.

15. An orthopedic implantable component adapted to replace a posterior element of a vertebra, wherein the vertebra comprises a vertebral body, a pair of pedicles extending posteriorly from said vertebral body, a lamina extending from said pedicles, a pair of superior facets extending from said pedicles, a pair of inferior facets extending from said lamina, a pair of pars interarticularis connecting superior and inferior facets, a spinous process extending from said lamina and a pair of transverse processes extending from said pedicles comprising:
a body adapted to be attached to a posterior location of said vertebra;
a male articulation member extending from said body; and
a female articulation member formed within said body.

16. The orthopedic implantable component of claim 15 wherein said body is configured to replace said lamina, said spinous process, said pars interarticularis, and said superior and inferior facets of said vertebra.

17. The orthopedic implantable component of claim 15 wherein said male articulation member comprises a hook.

18. The orthopedic implantable component of claim 15 wherein said female articulation member comprises a bar connecting opposite sides of a cavity formed within a bottom surface of said body.

19. The orthopedic implantable component of claim 15 wherein said body is attached to said pedicles of said vertebra.

20. The orthopedic implantable component of claim 19 wherein said body is attached to said pedicles via screws threaded through apertures formed in said body.

21. The orthopedic implantable component of claim 20 wherein said screws comprise a material selected from a group consisting of stainless steel, titanium, gold, silver, alloys thereof, plastic, absorbable and biodegradable material.

22. The orthopedic implantable component of claim 20 comprising a material selected from a group consisting of metal, plastic, ceramic, bone, polymers, composites, absorbable material, biodegradable material, and combinations thereof.

23. A spine stabilization method articulately connecting a first vertebra to a second vertebra comprising:
providing a first component wherein said first component comprises a body and at least one male articulation member attached to said first component body;
attaching said first component to a posterior location of said first vertebra;
providing a second component wherein said second component comprises a body and at least one female articulation member attached to said second component body;
attaching said second component to a posterior location of said second vertebra; and
articulately connecting said first component to said second component by engaging said at least one male articulation member to said at least one female articulation member.

24. The spine stabilization method of claim 23 wherein said first and second components are attached to said posterior locations of said first and second vertebra, respectively, via screws.

25. The spine stabilization method of claim 23 wherein said first and second components are attached to said posterior locations of said first and second vertebra, respectively, via hooks.

26. The spine stabilization method of claim 23 wherein said first component is articulately connected to said second component along a posterior midline of said first and second vertebrae.

27. The spine stabilization method of claim 23 wherein said first component is articulately connected to said second component along an axis medial to said facets of said vertebrae.

28. A spine stabilization method connecting a first vertebra to a second vertebra comprising:
attaching first and second screws to first and second locations, respectively, of said first vertebra;
attaching third and fourth screws to first and second locations, respectively, of said second vertebra;
providing a first component comprising a body and at least one male articulation member attached to said first component body and a second components comprising a body and at least one female articulation member attached to said second component body and articulately connecting said first component to said second component by engaging said at least one male articulation member to said at least one female articulation member;

attaching said body of said first component to said first and second locations of said first vertebra via said first and second screws, respectively;

attaching said body of said second component to said first and second locations of said second vertebra via said third and fourth screws, respectively; and tightening of all said screws.

29. The spine fixation method of claim 28 further comprising before attaching said bodies of said first and second components adjusting the width of said bodies of said first and second components.

* * * * *